US00PP17509P2

(12) United States Plant Patent
Olesen

(10) Patent No.: US PP17,509 P2
(45) Date of Patent: Mar. 20, 2007

(54) MINIATURE ROSE PLANT NAMED 'POULPAH033'

(50) Latin Name: ***Rosa* hybrid**
Varietal Denomination: Poulpah033

(75) Inventor: Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 85 days.

(21) Appl. No.: 11/240,013

(22) Filed: Sep. 29, 2005

(51) Int. Cl.
*A01H 5/00* (2006.01)

(52) U.S. Cl. ..... Plt./122

(58) Field of Classification Search ..... None
See application file for complete search history.

*Primary Examiner*—Kent Bell
*Assistant Examiner*—June Hwu

(57) ABSTRACT

A new miniature rose plant that has abundant, light red flowers and attractive foliage. The variety successfully propagates from softwood cuttings and is suitable for year-round production in commercial glasshouses. This new and distinct variety has shown to be uniform and stable in the resulting generations from asexual propagation.

2 Drawing Sheets

Botanical designation: *Rosa* hybrid.
Variety denomination: 'Poulpah033'.

SUMMARY OF THE INVENTION

The present invention constitutes a new and distinct variety of miniature rose plant which originated from a controlled crossing between the female seed parent 'Poulhi008' described in illustrated in U.S. Plant Pat. No. 15,722, and the male pollen parent, an unnamed seedling.

The two parents were crossed during the summer of 2002 and the resulting seeds were planted in a controlled environment in Fredensborg, Denmark. The new variety, named 'Poulpah033', originated as a single seedling from the stated cross.

The new variety may be distinguished from its female seed parent by the following combination of characteristics:

1. Flowers of the seed parent have a general tonality of Red-Purple Group 62C, while flowers of 'Poulpah033' are Red-Purple Group N57A to N66A.
2. 'Poulhi008' has a petal count of 40 to 45 petals while 'Poulpah033' has 35 to 40 petals.

The new variety may be distinguished from its male pollen parent by the following combination of characteristics:

1. The pollen parent has dark to medium red flowers while 'Poulpah033' has light red flowers.
2. The pollen parent has 75 to 80 petals, while 'Poulpah033' has 35 to 40 petals.

The objective of the hybridization of this rose variety for commercial culture was to create a new and distinct variety with unique qualities, such as:

1. Uniform and abundant dark pink flowers;
2. Vigorous and compact growth.
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventors, and distinguish 'Poulpah033' from all other varieties of which we are aware.

As part of the rose development program, Mogens N. Olesen germinated the seeds from the aforementioned hybridization and conducted evaluations on the resulting seedlings in a controlled environment in Fredensborg, Denmark. 'Poulpah033' was selected by the inventor as a single plant from the progeny of the hybridization in April 2003.

Asexual reproduction of 'Poulpah033' by cuttings and traditional budding was first done by Mogens N. Olesen in the nursery in Fredensborg, Denmark in 2003. This initial and other subsequent propagations conducted in controlled environments have demonstrated that the characteristics of 'Poulpah033' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'Poulpah033'. Specifically illustrated in the drawings:

FIG. 1.1; Open flowers;

FIG. 1.2; Flower bud closed, and partially open;

FIG. 1.3; Sepals, receptacle, pedicel, and reproductive flower parts;

FIG. 1.4; Flower petals, detached;

FIG. 2.1; Mature leaves;

FIG. 2.2; Bare stem;

FIG. 2.3; Juvenile stem and leaves exhibiting anthocyanin.

DETAILED DESCRIPTION OF THE VARIETY

The following is a description of 'Poulpah033', as observed in its growth in glasshouses in Fredensborg, Denmark. Observed plants are 4 months of age and were cultivated in 12 cm pots. Color references are made using The Royal Horticultural Society (London, England) Colour Chart, 2001, except where common terms of color are used.

For a comparison, several physical characteristics of the rose variety 'Poulac016', U.S. Plant Pat. No. 15,784 are compared to 'Poulpah033' in Chart 1.

CHART 1

| | 'Poulpah033' | 'Poulac016' |
|---|---|---|
| Petalage: | 35 to 40 petals | 100 petals |
| Flower Diameter: | 60 to 80 mm | 46 mm |
| General Tonality of Flower Color: | On open flower Red-Purple Group N57A to N66A. | Red-Purple Group 57A (RHS Colour Chart, 1995) |

FLOWER AND FLOWER BUD

Blooming habit: Continuous.

Flower bud:

*Size.*—Upon opening, 25 mm in length from base of receptacle to end of bud. 11 mm in diameter.

*Bud form.*—Broad-based ovate.

*Bud color.*—As sepals unfold, petals are Red-Purple Group N57A to N66A.

*Sepals.*—Upper Surface: Color: Green Group 138A. Apex is Yellow-Green Group 147A. Anthocyanic pigments Greyed-Orange Group 176A. Texture: Abundant to moderately abundant pubescence. Lower Surface: Color: Yellow-Green Group 144A. with anthocyanic intonations the color of Greyed-Orange 176A. Texture: Smooth with many stipitate glands. Shape: Apex: Cirrhose. Base: Flat at union with receptacle. Margins: Margins have strong foliaceous appendages on three of the five sepals. Size: 30 mm long by 7 mm wide.

*Receptacle.*—Surface Texture: Smooth. Shape: Urn-shaped. Size: 5 mm (h)×6 mm (w). Color: Yellow-Green Group 144B.

*Pedicel.*—Surface: Rough with stipitate glands. Length: 25 to 35 mm. Diameter: Normally 3 mm. Color: Yellow-Green Group 144A. Strength: Strong, erect. Scent: Stipitate glands, located on the pedicel exude a strong, sweet pine scent when touched.

*Borne.*—Normally singularly.

Flower bloom:

*Fragrance.*—Light floral scent.

*Duration.*—As a pot plant, flowers last up to 28 days. Petals do not fall cleanly away from plant.

*Size.*—Depth is 30 to 35 mm. Diameter is 60 to 80 mm when open.

*Form.*—Calathiform rosette with imbricated petal arrangement.

*Shape of flower, side view.*—Upon opening, the upper portion is flat, lower portion is flat. After opening, the upper portion is flattened convex. The lower portion is concave.

Petalage: There are normally 35 to 40 petals under normal conditions, 1 to 3 of which are petaloids.

Color:

*Upon opening, petals.*—Outermost petals: Upper Surface: Red-Purple Group N57A to N66A with occasional streaking the color of White Group 155B. Lower Surface: Red-Purple Group N57A to 58A with occasional streaking the color of White Group 155B. Innermost petals: Upper Surface: Red-Purple Group N57A to N66A with occasional streaking the color of White Group 155B. Lower Surface: Red-Purple Group N57A to 58A with occasional streaking the color of White Group 155B.

*Upon opening, basal petal spots.*—Upper Surface: Yellow Group 3C. Lower Surface: Yellow Group 2D.

*After opening, petals.*—Outermost petals: Upper Surface: Red-Purple Group N57A with occasional streaks the color of White Group N155B. Lower Surface: Red-Purple Group 63 A to 58B with occasional streaks the color of White Group N155B. Innermost petals: Upper Surface: Red-Purple Group N57A with occasional streaks the color of White Group N155B. Lower Surface: Red-Purple Group 63A to 58B with occasional streaks the color of White Group N155B.

*After opening, basal petal spots.*—Upper Surface: Yellow-Group 3C. Lower Surface: Yellow Group 2D.

General tonality: On open flower Red-Purple Group N57A to N66A. No change in the general tonality as flowers reach full maturity.

Petals:

*Petal reflex.*—Strong.

*Petal margin.*—Entire.

*Shape.*—Broad elliptical. Base: Acute. Apex: Rounded.

*Size.*—Petal size varies. Outer petals: 40 mm (l)×40 mm (w). Inner petals: 30 mm (l)×25 mm (w).

*Thickness.*—Average.

*Texture.*—Smooth.

Petaloids:

*Quantity.*—Normally, 1 to 3.

*Size.*—15 mm long; 8 mm wide.

*Shape.*—Irregular, narrow elliptical with acute base and rounded apex.

*Color.*—Upper surface: Red Group 45B. Lower surface: Red Group 46A and B.

Reproductive organs:

*Pollen.*—None observed.

*Anthers.*—Size: 2–5 mm long. Color: Greyed-Yellow Group 160B. Quantity: 90 to 100.

*Filaments.*—Color: Base: Greyed-Orange Group 163B. Upper: Greyed-Orange Group N163B. Length: 5 to 6 mm.

*Pistils.*—Length: 7 mm long. Quantity: 30 to 40.

*Stigmas.*—Inferior in their position relative to the length of the filaments and the height of the anthers. Color: Greyed-Yellow Group 162A.

*Styles.*—Color: Red-Purple Group 61C.

*Seed formation.*—Seed formation not observed on potted greenhouse plants.

PLANT

Plant growth: Moderate, upright, compact and bushy. When grown as a 15 cm pot plant on its own roots, the average height of the plant itself is 20 to 25 cm and the average width is 20 cm.

Stems:

*Color.*—Young wood: Yellow-Green Group 144B. Older wood: Yellow-Green Group 146A.

*Internodal distance.*—25 mm.

*Length of stems.*—15 cm from the base of the stem to the flowering portion.

*Surface texture.*—Young wood: Smooth. Older wood: Smooth.

Thorns:

*Incidence.*—7 mm per 10 cm of stem.

*Size.*—Average length: 6 mm.

*Color.*—Juvenile thorns are Greyed-Yellow Group 161D. Mature thorns are Greyed-Yellow Group 161D.

*Shape.*—Upper side: Flat. Lower side: Concave.

Plant foliage: Normal number of leaflets on normal leaves in middle of the stem: 5 leaflets.

*Compound leaf size.*—85 mm (l)×65 mm (w).

*Quantity.*—4 leaves per 10 cm of stem.

*Color.*—Juvenile foliage: Upper Leaf Surface: Yellow-Green Group 146A. Lower Leaf Surface: Yellow-Green Group 146B. Mature foliage: Upper Leaf Surface: Yellow-Green Group 147A. Lower Leaf Surface: Yellow-Green Group 148B.

Plant leaves and leaflets:

*Stipules.*—Size: Normally 8 mm. Shape: Linear, slightly broad based with outward extending apecies. Margins: Finely serrated with stipitate glands. Color: Yellow-Green Group 144A to 146B.

*Petiole.*—Length: Normally 13 mm. Diameter: 1.5 mm. Upper Surface: Color: Yellow-Green Group 144A to 146B. Anthocyanin: Greyed-Purple Group 187A to 187B. Underneath: Few stipitate glands observed. Lower Surface: Color: Yellow-Green Group 146B. Underneath: 2 to 3 mm prickles observed.

*Rachis.*—Size: Normally 25 mm. Upper Surface: Color: Yellow-Green Group 144A to 146B. Anthocyanin: Greyed-Purple Group 187A to 187B. Underneath: Few stipitate glands observed. Lower Surface: Color: Yellow-Green Group 146B. Underneath: 2 to 3 mm prickles observed.

*Leaflet.*—Size: Normally 45 to 50 mm in length by 30 to 33 mm wide. Edge: General Shape: Ovate. Apex Shape: Acute. Base Shape: Rounded. Texture: Smooth. Thickness: Average. Arrangement: Odd pinnate. Venation: Reticulate. Leaf Gloss: Very glossy.

Disease resistance: Average resistance to powdery mildew, black spot, and *Botrytis* under normal growing conditions in Fredensborg, Denmark.

It is claimed:

1. A new and distinct variety of rose plant of the miniature class named 'Poulpah033', substantially as illustrated and described herein, due to its abundant, light red flowers, vigorous growth, compact habit, suitability for production from softwood cuttings in pots, and durable flowers and foliage that make the variety suitable for distribution in the floral industry.

* * * * *

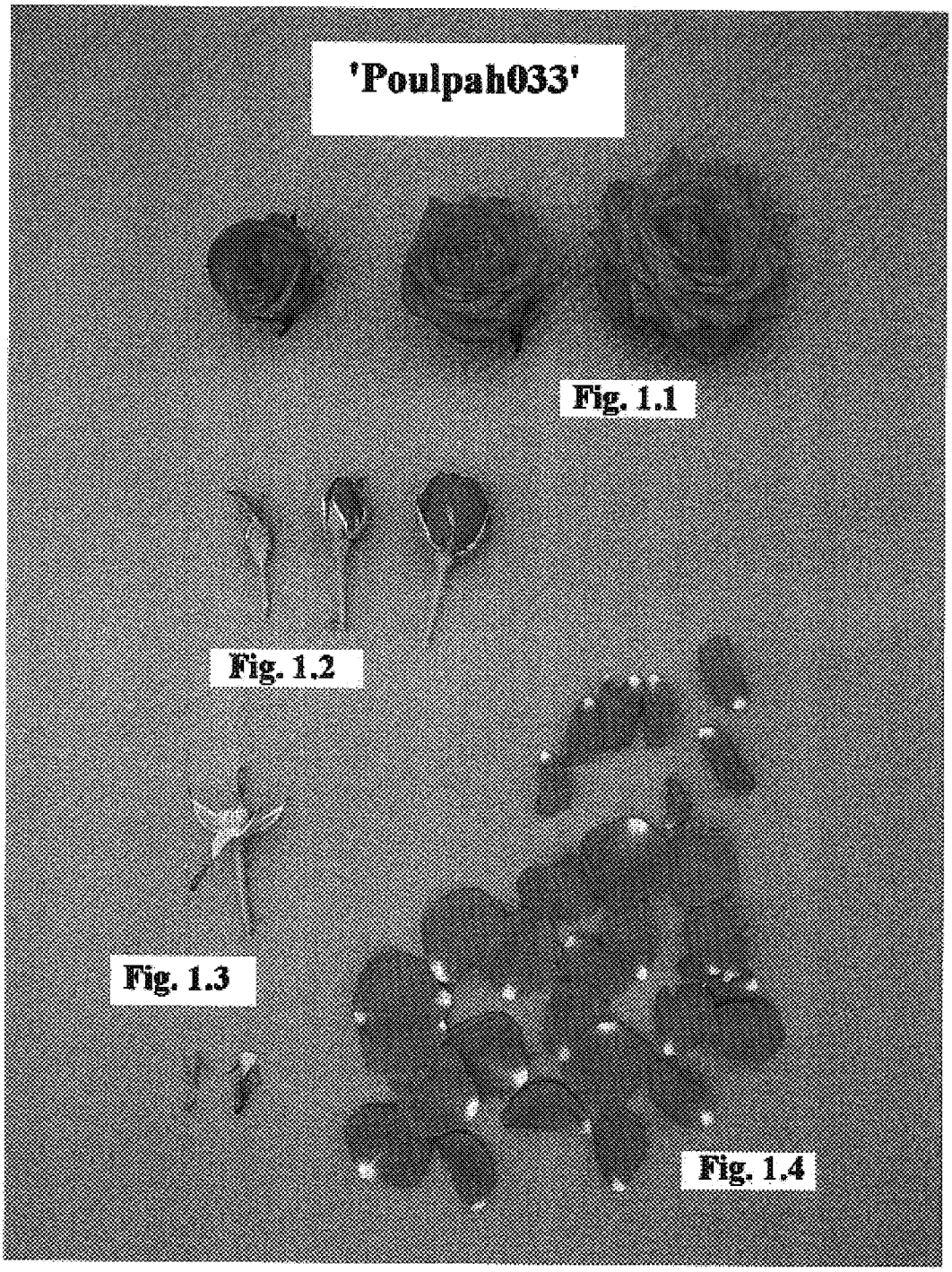
'Poulpah033'
Fig. 1.1
Fig. 1.2
Fig. 1.3
Fig. 1.4

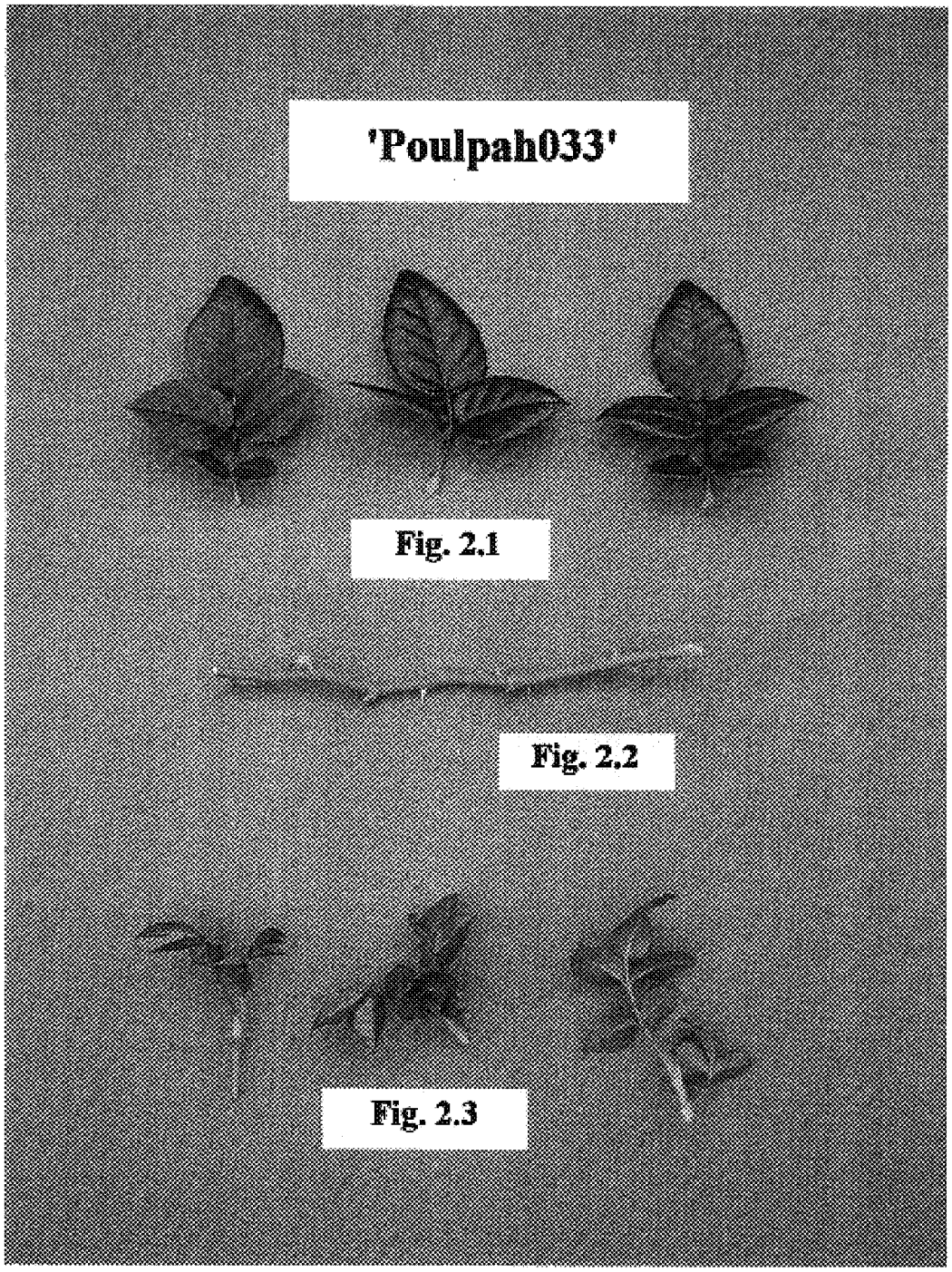
'Poulpah033'
Fig. 2.1
Fig. 2.2
Fig. 2.3